United States Patent [19]

Hamprecht

[11] 4,096,181
[45] Jun. 20, 1978

[54] SUBSTITUTED SULFAMIC ACID HALIDES

[75] Inventor: Gerhard Hamprecht, Mannheim, Germany

[73] Assignee: BASF Aktiengesellschaft, Ludwigshafen, Germany

[21] Appl. No.: 735,897

[22] Filed: Oct. 26, 1976

[30] Foreign Application Priority Data

Nov. 28, 1975 Germany .............................. 2553460

[51] Int. Cl.$^2$ ................. C07C 143/14; C07C 143/70; C07C 143/21
[52] U.S. Cl. ............................ 260/543 R; 260/543 F
[58] Field of Search ............. 260/543 R, 513.6, 543 F

[56] References Cited

U.S. PATENT DOCUMENTS 3,992,444  11/1976  Hamprecht et al. ............. 260/543 R

FOREIGN PATENT DOCUMENTS 1,085,980  2/1954  France .............................. 260/543 R
1,121,060  1/1962  Germany ........................ 260/543 R
2,401,819  7/1975  Germany ........................ 260/543 R Primary Examiner—Norman Morgenstern
Attorney, Agent, or Firm—Keil, Thompson & Shurtleff

[57] ABSTRACT

New sulfamic acid halides and a process for the manufacture of sulfamic acid halides by reacting sulfamic acids with formaldehyde and acid halides. The products are starting materials for the manufacture of crop protection agents, dyes and pharmaceuticals.

11 Claims, No Drawings

SUBSTITUTED SULFAMIC ACID HALIDES

The invention relates to new sulfamic acid halides and to a process for the manufacture of sulfamic acid halides by reacting sulfamic acids with formaldehyde and acid halides.

The manufacture of N-alkylamidosulfonyl chlorides by reacting monoalkylammonium chlorides with sulfuryl chloride has been disclosed (Acta Chem. Scand. 17 (1963), 2141). when the reaction is carried out in the presence of a stronly polar, organic solvent, with the addition of a metal halide as the catalyst, the yields are improved (German Pat. No. 1,242,627). Whilst the process gives good yields in the case of lower, non-branched alkylamidosulfonyl chlorides, the yields decrease substantially if the alkyl radical is branched, and as its chain length is increased. The above method also cannot be used to manufacture haloalkylaminosulfonyl halides. A further disadvantage is the long reaction time which the process requires in order to give a satisfactory yield. In industrial operation, particularly, these processes present difficulties in working up, including environmental problems, due to the high chlorine content of the by-products. German Laid-Open Application DOS No. 1,943,233 discloses a process for the manufacture of β-chloroethylaminosulfonyl fluoride by halogen exchange of the corresponding aminosulfonyl chloride with hydrogen fluoride, under superatmospheric pressure. Bearing in mind the reaction conditions required, and the fact that the reaction is carried out in two stages, via the sulfonyl chloride first produced, the process is unsatisfactory from the point of view of simple and economical operation, particularly on an industrial scale.

The manufacture of N,N-dimethylaminosulfonyl chloride by reacting sulfuryl chloride with dimethylamine has been disclosed (Chemische Berichte, 14 (1881), 1,810–1,812). Particularly on an industrial scale, the process is involved and uneconomical, and gives unsatisfactory yields. N-Haloalkyl compounds cannot be manufactured by this method.

German Published Application DAS No. 1,028,129 discloses the manufacture of N,N-dialkylsulfamic acid chlorides by reacting secondary N-chloramines with sulfur dioxide. The manufacture of such sulfamic acid chlorides by reacting dialkylcarbamic acid chlorides with sulfur trioxide has also been disclosed (German Pat. No. 946,710). However, substituted alkyl derivatives are not obtainable by either process. Whilst the reaction of N-chloro-N,N-dialkylamines with sulfur dioxide is difficult to carry out industrially because the chloramines tend to decompose abruptly, the reaction of sulfur trioxide with dialkylcarbamic acid chlorides can only be used in the case of unsubstituted acid chloride starting materials of a low number of carbon atoms, because of the powerful oxidizing action of the sulfur trioxide.

It is an object of the present invention to provide a new process whereby hitherto inaccessible N-disubstituted sulfamic acid halides can be manufactured simply and economically, and in high yield and purity.

It is a further object of the present invention to provide the new sulfamic acid halides.

I have found that these objects are achieved and that sulfamic acid halides of the formula

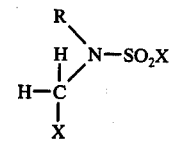

where R is an aliphatic or cycloaliphatic radical and each X is halogen, are obtained advantageously when sulfamic acid components of the formula

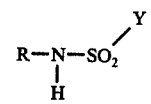

where R has the above meanings and Y is hydroxyl or halogen, are reacted with formaldehyde and an acid halide of phosphoric acid, or phosphorus acid or of carbonic acid, thionyl chloride, sulfur tetrafluoride and-/or sulfur dichloride.

Further, I have found the new sulfamic acid halides of the formula

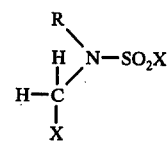

where each X is halogen and R is a cycloaliphatic radical or is an aliphatic radical which is not substituted by halogen atoms, or which is substituted by one or more halogen atoms at the carbon atom in the α-position, γ-position and/or even more remote positions relative to the nitrogen atom.

Preferred end products I I have found are the new sulfamic acid halides of the formula

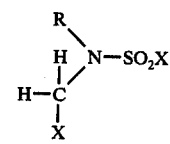

where R is alkyl of 1 to 20 carbon atoms which is unsubstituted or is substituted by one or more chlorine atoms at the carbon atom in the α-position, γ-position and/or even more remote positions relative to the nitrogen atom, or is cycloalkyl of 4 to [carbon atoms and X is bromine or chlorine.

Where methylsulfamic acid and methylsulfamic acid chloride are used with formaldehyde and thionyl chloride, the reactions can be represented by the following equations:

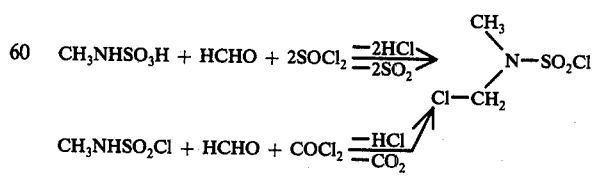

Compared to the prior art, the process of the invention provides hitherto inaccessible N-disubstituted sulfamic acid halides in a simple and economical manner, in high yield and purity. The reaction time is short and the working up of the reaction mixture — particularly with regard to protection of the environment — is simple and safe. In contrast to the acid halides mentioned, sulfuryl chloride is not a suitable reactant. Starting materials II where alkyl is of a higher number of carbon atoms can also be reacted by the process of the invention. All these advantageous results are surprising in view of the prior art.

Preferred starting materials II and, accordingly, preferred end products I are those where R is straight or branched alkyl or haloalkyl, especially chloroalkyl or bromoalkyl, of 1 to 20, especially 1 to 8, carbon atoms, or is cycloalkyl of 4 to 8 carbon atoms, X is fluorine or, especially, chlorine or bromine and Y is hydroxyl or fluorine or, especially, chlorine or bromine. The acid radicals may additionally be substituted by groups and/or atoms which are inert under the reaction conditions, eg. chlorine, bromine, alkyl of 1 to 4 carbon atoms or carbalkoxy of 2 to 4 carbon atoms.

Preferred starting materials II are methylsulfamic acid, ethylsulfamic acid, n-propylsulfamic acid, isopropylsulfamic acid, n-butylsulfamic acid, isobutylsulfamic acid, sec.-butylsulfamic acid, tert.-butylsulfamic acid, pentylsulfamic acid, pentyl-(3)-sulfamic acid, cyclopentylsulfamic acid, hexylsulfamic acid, cyclohexylsulfamic acid, heptylsulfamic acid, 1,2-dimethylbutylsulfamic acid, 1,3-dimethylbutylsulfamic acid, 2-chloropropylsulfamic acid, 3-chloropropylsulfamic acid, 2-chloroisopropylsulfamic acid, 1-(chloromethyl)-propyl-(1)-sulfamic acid, 2-chloro-2-methyl-propyl-(1)-sulfamic acid, tert.-amylsulfamic acid, 2-chloroethylsulfamic acid, 1-chloropropyl-(2)-sulfamic acid, 3-chlorobutyl-(4)-sulfamic acid, 1-chlorobutyl-(2)-sulfamic acid and 2-chlorobutyl-(3)-sulfamic acid and analogous sulfamic acid bromides, sulfamic acid fluorides and, especially, sulfamic acid chlorides.

Compounds which form formaldehyde under the reaction conditions, in particular paraformaldehyde and trioxane, may be used in place of formaldehyde.

The starting materials II can be reacted with formaldehyde in stoichiometric amount or using an excess, preferably in a ratio of from 1 to 4 moles, especially 1.1 to 1.5 moles, of formaldehyde per mole of starting material II. In the case of sulfamic acids with fairly long or branched chains, eg. of at least 4 carbon atoms, suitable amounts to use are from 1.5 to 4 moles of formaldehyde per mole of starting material II. The starting materials II can be reacted with the acid halide in stoichiometric amount or using an excess of acid halide, preferably — in the case of a sulfamic acid II — using a ratio of from 2.2 to 4 moles of acid halide per mole of sulfamic acid starting material II and from 1.1 to 2 moles of acid halide per mole of sulfamic acid halide starting mateial II. Preferred acid halides are thionyl chloride, phosphorus pentachloride, phosphorus trichloride, phosphorus oxychloride, phosphorus pentabromide, phosphorus tribromide, phosgene, sulfur tetrafluoride and sulfur dichloride.

As a rule, the reaction is carried out at from −40° to 120° C, especially from 10° to 100° C, under atmospheric or superatmospheric pressure, continuously or batchwise. Advantageously, solvents which are inert under the reaction conditions are used. Examples of suitable solvents are halohydrocarbons, especially chlorohydrocarbons, eg. tetrachloroethylene, 1,1,2,2- or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene o-, p- and m-dichlorobenzene, o-, p- and m-dibromobenzene, o-, m- and p-chlorotoluene, 1,2,4-trichlorobenzene, 1,10-dibromodecane and 1,4-dibromobutane, ethers, eg. ethyl propyl ether, methyl tert.-butyl ether, n-butyl ethyl ehter, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-di-chlorodiethyl ether, nitro hydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic or cycloaliphatic hydrocarbons, eg. heptane, pinane, nonane, o-, m- and p-cymene, gasoline fractions with boiling ranges of from 70° to 190° C, cyclohexane, methylcyclohexane, decalin, petroleum ether, hexane, naphtha, 2,2,4-trimethylpentane, 2,2,3-trimethylpentane, 2,3,3-trimethylpentane and octane, and appropriate mixtures. The amount of solvent used is advantageously from 100 to 2,000 percent by weight, preferably from 400 to 1,200 percent by weight, based on starting material II.

The reaction is suitably carried out in the presence of an acid, advantageously in the presence of from 0.5 to 10, especially from 1 to 3, moles of acid per mole of starting material II. The acids may be inorganic or organic. Instead of monobasic acids, equivalent amounts of polybasic acids may be used. Examples of suitable acids are hydrogen chloride, hydrogen bromide, hydrogen iodide, hydrogen fluoride, sulfuric acid, phosphoric acid, sulfonic acids, eg. benzenesulfonic acid and p-toluenesulfonic acid, acids containing boron, eg. boric acid and fluoboric acid, aliphatic carboxylic acids, eg. chloroacetic acid, dichloroacetic acid, trichloroacetic acid, cyanoacetic acid, acetic acid, propionic acid, butyric acid and isobutyric acid, or appropriate mixtures. The acids may be used in a concentrated form, as mixtures with one another and/or as mixtures with a solvent. Hydrogen chloride, sulfuric acid, phosphoric acid and hydrogen bromide are preferred.

Lewis acids, advantageously in an amount of from 0.01 to 0.04 mole per mole of starting material III, may also be added as acids in order to accelerate the reaction. For the purposes of the invention, Lewis acids are electrophilic compounds with an incomplete electron configuration, which can take up an electron pair of a base. For a definition of Lewis acids, reference may be made to Houben-Weyl, Methoden der organischen Chemie, Volume 4/2, page 6, and Rodd, Chemistry of Carbon Compounds, Volume IA, page 103 (Elsevier Publ. Co., N.Y. 1951). Advantageous Lewis acids to use are halides, especially chlorides, of metals of groups 2 to 6 and 8 of the periodic table, eg. zinc chloride, boron chloride, aluminum chloride, iron chloride, tin chloride, titanium chloride, antimony chloride, bismuth chloride, molybdenum chloride, tungsten chloride, aluminum bromide and boron trifluoride. The Lewis acids may also be used in the form of their complexes, eg. boron trifluoride etherate, fluoboric acid, boron fluoride/a- cetic acid, boron fluoride/diacetic acid, boron fluoride/phosphoric acid and boron trichloride complexes with phosphorus trichloride and phosphorus oxychloride. Preferred catalysts are iron(III) chloride, zinc(II) chloride and aluminum(III) chloride. In some cases it is advantageous to use a combination of the said catalysts.

The halogenation catalyst used is advantageously a carboxylic acid amide disubstituted at the nitrogen atom, a tertiary amine or a carbamic acid halide disubstituted at the nitrogen atom, especially carbamic acid chloride, advantageously in an amount of from 0.2 to 6 percent by weight, based on starting material II. Mixtures of the said catalysts may also be used for the reaction. The amine may also be a diamine, or may be used in the form of appropriate salts, eg. amine hydrochlorides, or quaternary salts. Preferred catalysts are trimethylamine, triethylamine, pyridine, N,N-dimethylaniline, N,N-diethylaniline, N-ethylpiperidine, N-methylpyrrolidine, α-, β- and γ-picoline, N-propylpiperidine, quinoline, isoquinoline, quinazoline, quinoxaline, triamylamine, tri-n-butylamine, n-propyldiisopropylamine, trifurfurylamine, trihexylamine, N-methylimidazole, N-methylpyrrole, 2,6- and 2,4-lutidine, N-(4-pyridyl)-pyridinium chloride hydrochloride, triethylenediamine, p-dimethylaminopyridine, N-dimethylcyclohexylamine, pyrimidine and acridine, dimethylformamide, diethylformamide, formic acid N-methylanilide, N,N-dimethylacetamide, N-methylpyrrolidone and tetramethylurea, dimethyl-, diethyl-, di-n-propyl-, diisopropyl-, di-n-butyl-, diisobutyl-, di-sec.-butyl-, di-tert.-butyl-, dipentyl-, di-(pentyl-2)-, di-(pentyl3)-, di-n-hexyl-, di-n-heptyl-, di-n-octyl-, di-n-nonyl- and di-n-decyl-carbamic acid chloride, or corresponding catalyst compounds containing 2 or 3 of the above radicals which, however, are different from one another, eg. dimethylethylamine, N-methyl-N-ethylformamide or N-methyl-N-ethylcarbamic acid chloride. At times, appropriate catalysts may also simultaneously serve as the solvent or reaction medium.

The reaction may be carried out as follows: a mixture of the starting material II, formaldehyde and the halide, if appropriate together with catalyst and/or solvent, is kept at the reaction temperature for from 3 to 8 hours. It is possible first to mix the halide or the starting material II with the solvent and then to add the other components. The end product I is isolated from the reaction mixture by conventional methods, for example by fractional distillation.

In a preferred embodiment of the process of the invention, a suspension of the starting material II is reacted with formaldehyde in an inert solvent for from 5 to 60 minutes at from 50° to 100° C, and after the mixture has cooled to from 5° to 20° C, the halide is then added, where appropriate after first having added a catalytic amount of a halogenation catalyst. The duration and temperature of addition of the halide is advantageously selected substantially in accordance with the rate at which the gases are eliminated. In general, the acid chloride is initially added slowly. When the elimination of gas slows down, it is advantageous to accelerate the reaction by heating, advantageously at from 60° to 120° C, depending on the boiling point of the solvent used.

In a further advantageous embodiment of the process of the invention, the components are suspended in an inert solvent and the reaction is then assisted by adding an acid catalyst; for example, the reaction mixture is saturated with a hydrogen halide at from −20° to 60° C, the halide is then added and the reaction is carried out in the above manner.

The new compounds which may be manufactured by the process of the invention are valuable starting materials for the manufacture of crop protection agents, dyes and pharmaceuticals. Thus, extremely selective herbicides may be manufactured from the end products I of the invention by reaction with glycollic acid anilides (German Laid-Open Application DOS No. 2,351,608). Hydrolysis of the end products I may be used to produce the corresponding haloamines, which are starting materials for chemotherapeutic agents for combating cancer and tumors (Ullmanns Encyklopädie der technischen Chemie, Volume 10, pages 773 et seq.). Using the processes disclosed in Arzneimittelforschung 12 (1962), 1,119 et seq. the end products I can be converted to haloalkyl-sulfamyl-hydrazones, which are active against sarcomas and carcinomas. Herbicidal sulfamic acid esters may be manufactured from the end products I by reaction with 2-alkoxy-2,3-dihydro-3,3-dimethyl-5-hydroxy-benzofuran derivatives (German Laid-Open Application DOS No. 2,324,592).

In the context of the uses enumerated, new end products I which are preferred are the sulfamic acid halides of the formula

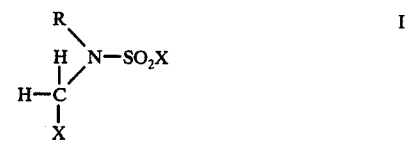

where R is alkyl of 1 to 20 carbon atoms which is unsubstituted or is substituted by one or more chlorine atoms at the carbon atom in the α-position, γ-position and/or even more remote positions relative to the nitrogen atom, or is cycloalkyl of 4 to 8 carbon atoms and X is bromine or chlorine, especially N-methyl-N-chloromethylsulfamic acid chloride, N-methyl-N-bromomethylsulfamic acid bromide, N-ethyl-N-chloromethylsulfamic acid chloride, N-butyl-N-chloromethylsulfamic acid chloride, N-isopropyl-N-chloromethylsulfamic acid chloride, N-n-hexyl-N-chloromethylsulfamic acid chloride, N-n-propyl-N-chloromethylsulfamic acid chloride, N-cyclohexyl-N-chloromethylsulfamic acid chloride and N-β-chloroethyl-N-chloromethylsulfamic acid chloride.

In the Examples which follow, parts are by weight.

EXAMPLE 1

(a) A suspension of 22.2 parts of methylsulfamic acid and 7.5 parts of paraformaldehyde in 300 parts of 1,2-dichloroethane is saturated with hydrogen chloride (22 parts) at from 10° to 15° C, whilst stirring. 0.05 part of pyridine and 59.5 parts of thionyl chloride are then added in the course of 10 minutes at from 20° to 25° C, whereupon a vigorous evolution of gas commences. The reaction mixture is stirred for 2 hours at from 20° to 25° C and from 4 hours under reflux (83° C) and is then concentrated under reduced pressure. Distillation of the residue gives 12 parts (34% of theory) of N-methyl-N-chloromethylsulfamic acid chloride of boiling point 49°–59° C/0.05 mbar and $n_D^{25} = 1.4813$.

(b) 27.8 parts (78% of theory) of N-methyl-N-chloromethylsulfamic acid chloride are obtained under the same reaction conditions, but using 85.5 parts of phosphorus pentachloride instead of pyridine and thionyl chloride.

EXAMPLE 2

(a) A suspension of 66.6 parts of methylsulfamic acid, 27 parts of paraformaldehyde and 1 part of iron(III) chloride in 700 parts of chloroform is saturated with hydrogen chloride at from 0° to 10° C, whilst stirring. 250 parts of phosphorus pentachloride are then introduced in portions and the reaction mixture is stirred for 1 hour at room temperature and 2½ hours under reflux (62° C). It is then concentrated under reduced pressure, and distilled. 55.2 parts (52% of theory) of N-methyl-N-chloromethylsulfamic acid chloride of boiling point 48°–59° C/0.01 mbar and $n_D^{25} = 1.4800$ are obtained.

(b) Using the same reaction conditions without iron(III) chloride, with 350 parts of n-heptane as the solvent and 0.6 part of triethylenediamine as the halogenation catalyst, the same end product as above was obtained in the same yield and the same purity.

EXAMPLE 3

A suspension of 66 parts of methylsulfamic acid and 27 parts of paraformaldehyde in 600 parts of 1,2-dichloroethane is saturated with hydrogen chloride (60 parts) at from 10° to 15° C, whilst stirring. 325 parts of phosphorus tribromide are then added in the course of 20 minutes and the mixture is slowly heated to the reflux temperature. After having been heated for 5 hours at 83° C, the reaction mixture is concentrated under reduced pressure and distilled, giving 48 parts (30% of theory) of N-methyl-N-bromomethylsulfamic acid bromide of boiling point 75°–84° C/0.05 mbar.

EXAMPLE 4

A suspension of 93.8 parts of ethylsulfamic acid and 27 parts of paraformaldehyde in 650 parts of 1,2-dichloroethane is saturated with hydrogen chloride (72 parts) at from 10° to 15° C, whilst stirring. 0.2 part of pyridine and 142.8 parts of thionyl chloride are then added in the course of 15 minutes at 15° C. The reaction mixture is stirred for ½ hour at 25° C and 1½ hour under reflux. 83.5 parts of phosphorus pentachloride are then added and the mixture is stirred for 4 hours under reflux (83° C) until the evolution of gas has ceased. On concentrating under reduced pressure, and distilling, 84 parts (58% of theory) of N-ethyl-N-chloromethylsulfamic acid chloride of boiling point 70°–75° C/0.1 mbar and $n_D^{25} = 1.4800$ are obtained.

EXAMPLE 5

A suspension of 92 parts of n-butylsulfamic acid and 36 parts of paraformaldehyde in 500 parts of 1,2-dichloroethane is saturated with hydrogen chloride at from 10° to 15° C, whilst stirring. 0.2 part of pyridine and 250 parts of phosphorus pentachloride are now added in portions, at from 5° to 20° C. The reaction mixture is heated to the reflux temperature (83° C) in the course of 40 minutes and is then stirred for a further 1½ hours. After removing the solvent and excess phosphorus pentachloride under reduced pressure, 89 parts (68% of theory) of N-butyl-N-chloromethylsulfamic acid chloride of boiling point 80°–89° C/0.04 mbar and $n_D^{25} = 1.4760$ are obtained.

EXAMPLE 6

(a) 90 parts of isopropylsulfamic acid and 23.3 parts of paraformaldehyde in 600 parts of 1,2-dichloroethane are stirred for 15 minutes at 83° C. After the mixture has cooled to 15° C, 0.2 part of pyridine are added, followed by 271 parts of phosphorus pentachloride added in portions. The reaction mixture is heated to 83° C in the course of 45 minutes and is then stirred for a further 2 hours. After removing the solvent and excess phosphorus pentachloride under reduced pressure, 41 parts (31% of theory) of N-isopropyl-N-chloromethylsulfamic acid chloride of boiling point 83°–85° C/0.4 mbar and $n_D^{25} = 1.4805$ are obtained.

(b) If the suspension of isopropylsulfamic acid and paraformaldehyde in 1,2-dichloroethane is first saturated with hydrogen chloride at from 10° to 15° C and then reacted as described in Example 6 a), 100 parts (75% of theory) of N-isopropyl-N-chloromethylsulfamic acid chloride are obtained.

(c) If the suspension of isopropylsulfamic acid and paraformaldehyde in 1,2-dichloroethane is first saturated with hydrogen chloride at from 10° to 15° C and then mixed with 35 parts of dimethylcarbamic acid chloride as the solvent, and with 430 parts of phosgene added in the course of 11 hours, 80.7 parts (60.5% of theory) of N-isopropyl-N-chloromethylsulfamic acid chloride are obtained.

(d) If the suspension of isopropylsulfamic acid and paraformaldehyde in 300 parts of 1,2-dichloroethane is saturated with hydrogen chloride at from 10° to 15° C, a suspension of 67.5 parts of phosphorus pentachloride in 330 parts of phosphorus oxychloride is added in the course of 20 minutes at the same temperature, and the batch is stirred for 6 hours at from 90° to 96° C, 98.8 parts (74% of theory) of N-isopropyl-N-chloromethylsulfamic acid chloride are obtained.

EXAMPLES 7 AND 8

The following compounds are obtained by the method described in Example 5:

| Example | Parts | Starting material II | Parts | % of theory | End product I | Boiling point | $n_D^{25}$ |
|---|---|---|---|---|---|---|---|
| 7 | 69.5 | n-C$_3$H$_7$NHSO$_3$H | 71.5 | 69 | n-C$_3$H$_7$\N—SO$_2$Cl / Cl—CH$_2$ | 67–76° C/0.03 | 1.4806 |
| 8 | 36.2 | n-C$_6$H$_{13}$NHSO$_3$H | 20.5 | 41 | n-C$_6$H$_{13}$\N—SO$_2$Cl / Cl—CH$_2$ | 130° C/0.01 * | 1.4725 |

* Bath temperature of the thin film evaporator

EXAMPLE 9

A mixture of 64.8 parts of methylsulfamic acid chloride and 18.1 parts of paraformaldehyde in 400 parts of 1,2-dichloroethane is stirred for 4 minutes at room temperature. After adding 0.1 part of pyridine as the catalyst, 71.5 parts of thionyl chloride are added at the same temperature, whilst stirring. On heating the mixture, a vigorous evolution of gas commences at 35° C. The reaction mixture is stirred for 2 hours at from 50° to 55° C and for 2 hours at 83° C. The reaction solution is then evaporated under reduced pressure and the residue is distilled, giving 83.5 parts (94% of theory) of N-chloromethyl-N-methylsulfamic acid chloride (boiling point 49°–56° C/0.02 mbar $n_D^{25} = 1.4813$).

EXAMPLE 10

(a) A mixture of 96.9 parts of methylsulfamic acid chloride and 28.5 parts of paraformaldehyde in 500 parts of 1,2-dichloroethane is saturated with hydrogen chloride at from 5° to 15° C, whilst stirring. 5 parts of dimethylformamide are then added as the catalyst, after which 110 parts of phosgene are added in the course of 2 hours whilst raising the reaction temperature to 83° C. After removing excess phosgene and the solvent under reduced pressure, distillation at 54°–60° C/0.1 mbar gives 121 parts (91% of theory) of N-chloromethyl-N-methylsulfamic acid chloride of $n_D^{25} = 1.4820$.

(b) If 5 parts of dimethylcarbamoyl chloride are used as the catalyst, the same end product is obtained in the same yield and purity.

EXAMPLE 11

0.2 part of pyridine and 325 parts of phosphorus tribromide are added to a mixture of 129.4 parts of methylsulfamic acid chloride and 36.2 parts of paraformaldehyde in 750 parts of 1,2-dichloroethane whilst stirring at from 20° to 25° C. The reaction mixture is stirred for 5 hours at 83° C and then concentrated under reduced pressure. Distillation gives 170 parts (77% of theory) of N-bromomethyl-N-methylsulfamic acid chloride of boiling point 82°–94° C/0.2 mbar and $n_D^{25} = 1.5240$.

EXAMPLE 12

574.5 parts of N-ethylsulfamic acid chloride and 168.2 parts of paraformaldehyde in 1,500 parts of 1,2-dichloroethane are saturated with hydrogen chloride first for 30 minutes at 20° C and then for 20 minutes at from 50°–55° C, whilst stirring. After adding 0.3 part of pyridine, 620 parts of thionyl chloride are added in the course of 45 minutes at 20° C, whilt stirring. The reaction mixture is stirred for 2 hours at from 25° to 30° C and then for 2 hours at 83° C. After concentration under reduced pressure, and distillation, 667 parts (87% of theory) of N-chloromethyl-N-ethylsulfamic acid chloride of boiling point 61°–65° C/0.01 mbar and $n_D^{25} = 1.4780$ are obtained.

EXAMPLE 13

(a) A mixture of 39 parts of paraformaldehyde in 370 parts of 1,2-dichloroethane is saturated with hydrogen chloride gas at 10° C. After adding 171.6 parts of n-butylsulfamic acid chloride the solution is first saturated with hydrogen chloride gas for 20 minutes at from 50° to 55° C and then combined with 143 parts of thionyl chloride in the course of 20 minutes at 20° C, whilst stirring. The reaction mixture is then heated to 83° C in the course of 1 hour and stirred for a further hour at the same temperature. After concentration under reduced pressure, and distillation, 125 parts (57% of theory) of N-n-butyl-N-chloromethylsulfamic acid chloride of boiling point 90°–105° C/0.2 mbar and $n_D^{25} = 1.4770$ are obtained.

(b) If, in carrying out the same reaction, a suspension of 100 parts of phosphorus pentachloride in 370 parts of phosphorus oxychloride is added in place of thionyl chloride, and the mixture is stirred for 2 hours under reflux, 134 parts (61% of theory) of N-n-butyl-N-chloromethylsulfamic acid chloride are obtained. Dichloroethane and phosphorus oxychloride are recovered virtually quantitatively as the low-boiling fraction.

EXAMPLES 14 TO 18

The following compounds are obtained by the method described in Example 5:

| Example | Parts | Starting material | Parts | End product | Boiling point (° C/mbar) | $n_D^{25}$ |
|---|---|---|---|---|---|---|
| 14 | 157.6 | n-C₃H₇NHSO₂Cl | 165 | | 66–76° C/0.04 | 1.4808 |
| 15 | 157.6 | i-C₃H₇NHSO₂Cl | 157 | | 75–83° C/0.2 | 1.4812 |
| 16 | 33.4 | n-C₆H₁₃NHSO₂Cl | 36 | | 130° C/0.01 | 1.4725 |
| 17 | 83 | | 82 | | 112–117° C/0.04 | 1.5042 |
| 18 | 105 | Cl—CH₂CH₂NHSO₂Cl | 114 | | 90–105° C/0.01 | 1.5023 |

I claim:

1. Sulfamic acid halides of the formula

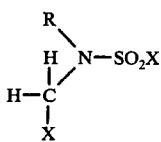

where each X is halogen and R is a cycloaliphatic radical or is an aliphatic radical which is not substituted by halogen atoms, or which is substituted by one or more halogen atoms at the carbon atom in the α-position, γ-position and/or even more remote positions relative to the nitrogen atom.

2. Sulfamic acid halides of the formula

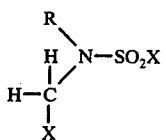

where R is alkyl of 1 to 20 carbon atoms which is unsubstituted or is substituted by one or more chlorine atoms at the carbon atom in the α-position, γ-position and/or even more remote positions relative to the nitrogen atom, or is cycloalkyl of 4 to 8 carbon atoms and X is bromine or chlorine.

3. N-Methyl-N-chloromethylsulfamic acid chloride.
4. N-Methyl-N-bromomethylsulfamic acid bromide.
5. N-Ethyl-N-chloromethylsulfamic acid chloride.
6. N-Butyl-N-chloromethylsulfamic acid chloride.
7. N-Isopropyl-N-chloromethylsulfamic acid chloride.
8. N-n-Hexyl-N-chloromethylsulfamic acid chloride.
9. N-n-Propyl-N-chloromethylsulfamic acid chloride.
10. N-Cyclohexyl-N-chloromethylsulfamic acid chloride.
11. N-β-Chloroethyl-N-chloromethylsulfamic acid chloride.

* * * * *